US006702809B1

United States Patent
Knopp et al.

(10) Patent No.: US 6,702,809 B1
(45) Date of Patent: *Mar. 9, 2004

(54) SYSTEM FOR DETECTING, MEASURING AND COMPENSATING FOR LATERAL MOVEMENTS OF A TARGET

(75) Inventors: Carl F. Knopp, San Mateo, CA (US); Jerzy Orkiszewski, Livermore, CA (US); Jan Wysopal, Livermore, CA (US); Hanna J. Hoffman, Palo Alto, CA (US)

(73) Assignee: Visx, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/172,976

(22) Filed: Oct. 14, 1998

Related U.S. Application Data

(63) Continuation of application No. 08/515,152, filed on Aug. 15, 1995, now Pat. No. 5,865,832, which is a continuation of application No. 08/019,550, filed on Feb. 19, 1993, now abandoned, which is a continuation-in-part of application No. 07/843,374, filed on Feb. 27, 1992, now abandoned, which is a continuation-in-part of application No. 07/475,657, filed on Feb. 6, 1990, now abandoned, and a continuation-in-part of application No. 07/305,315, filed on Feb. 6, 1989, now Pat. No. 5,098,426.

(51) Int. Cl.[7] .............................................. A61F 9/007
(52) U.S. Cl. ................................ 606/10; 606/5; 606/13; 351/210
(58) Field of Search .......................... 606/4–6, 10–13; 351/210–212; 356/45

(56) References Cited

U.S. PATENT DOCUMENTS

| 3,804,496 A | 4/1974 | Crane et al. |
| 4,411,519 A | * 10/1983 | Tagami .................... 356/45 |
| 4,443,075 A | 4/1984 | Crane |
| 4,571,712 A | * 2/1986 | Romano et al. .............. 369/44 |
| 4,848,340 A | 7/1989 | Bille et al. |
| 4,972,836 A | 11/1990 | Schenck et al. |
| 5,070,883 A | 12/1991 | Kasahara |
| 5,098,426 A | 3/1992 | Sklar et al. |
| 5,162,641 A | 11/1992 | Fountain |
| 5,231,674 A | 7/1993 | Cleveland et al. |
| 5,620,436 A | 4/1997 | Lang et al. |
| 5,632,742 A | 5/1997 | Frey et al. |

OTHER PUBLICATIONS

Bahill et al., "Variability and development of a normative data base for saccadic eye movements," *Invest. Ophthalmol. Vis. Sci.*, vol. 21, No. 1, Part 1, pp. 116–125, Jul. 1981.

Crane et al., "Generation–V dual–Purkinje–image eye–tracker", *Applied Optics*, vol. 24, No. 4, pp. 527–537, Feb. 1985.

Forster, Albert, "Correlation Tracking—A new technology applied to laser photocoagulation," *SPIE Ophthalmic Technologies*, vol. 1423, pp. 103–104 (1991).

Gormley et al., "Corneal modeling", *Cornea*, vol. 7, No. 1, pp. 30–35 (1988).

Millbocker et al., "Intensified charge–coupled–device–based eyetracker and image stabilizer," *Applied Optics*, vol. 31, No. 19, pp. 3719–3729, Jul. 1992.

Nguyen et al., "Slowed saccades in the acquired immunodeficiency," *American Journal of Ophthalmology*, vol. 107, pp. 356–360, Apr. 1989.

Young et al., "Major eye movement measurement techniques," Survey of eye movement recording methods, pp. 401–429.

\* cited by examiner

*Primary Examiner*—David M. Shay
(74) *Attorney, Agent, or Firm*—Townsend and Townsend and Crew LLP; Lynn M. Thompson

(57) ABSTRACT

A method, apparatus and system for a transverse tracker is described that can greatly improve the accuracy, speed, range, reliability, versatility, safety, and efficacy of interventions such as laser microsurgery, particularly ophthalmic surgery, and industrial micromachining. The instrument and system disclosed are applicable to those situations wherein the positioning accuracy of laser lesions is critical, and/or whenever precise operations on a target or series of targets subject to random movement during a procedure are to be effected. The present invention provides means for stabilizing the motion of targets in a plane perpendicular to the axial direction, thus allowing an imaging system, diagnostics illumination, and/or laser beam to maintain a lock on the target area, regardless of its movement. The invention also provides means for recording eye movements in real time and in which data can be stored and manipulated for the purpose of compensating for lateral target motion by either hardware or software means. Unique attributes provided in the tracking system include means for (1) sensing contrast in recognizable large scale boundaries such as the change between the cornea/sclera interface (limbus), thereby to determine the absolute location and orientation of these boundaries, all without having to resort to digital sampling techniques and (2) dual mode operation of an electronic control system compatible with all analog technologies, thereby substantially increasing the speed of operations over other, comparable digital method. The tracking system of the invention is at least comprised of illumination sources, imaging optics, a sensor such as a position-sensitive detector, a movable optical element such as a mirror, a two-dimensional logic board, and a dedicated microprocessor, including appropriate signal processing firmware and software. Additional optics can be incorporated to provide interface with other assemblies such as depth tracking, target viewing and/or laser surgery subsystems. The system of the invention affords considerable flexibility in selecting particular components such as the illuminators, detectors and servo devices, which, in turn, allows broad application of this system to tracking tasks in diverse medical surgical, diagnostic, and industrial settings.

10 Claims, 8 Drawing Sheets

$$X_{POS}(2\ \text{sensor}) = \frac{(A+B+C+D)-(A'+B'+C'+D')}{A+B+C+D+A'+B'+C'+D'}$$

$$Y_{POS}(2\ \text{sensor}) = \frac{(A+B+A'+B')-(C+D+C'+D')}{A+B+C+D+A'+B'+C'+D'}$$

$$X_{POS}(1\ \text{sensor}) = \frac{(A+C)-(B+D)}{A+B+C+D}$$

$$Y_{POS}(1\ \text{sensor}) = \frac{(A+B)-(C+D)}{A+B+C+D}$$

$$X_{POS} = \frac{A-C}{A+C}$$

$$Y_{POS} = \frac{B-D}{B+D}$$

SYSTEM FOR DETECTING, MEASURING AND COMPENSATING FOR LATERAL MOVEMENTS OF A TARGET

REFERENCE TO RELATED APPLICATIONS

This application is a continuation of U.S. patent application Ser. No. 08/515,152, filed Aug. 15, 1995 now U.S. Pat. No. 5,865,832, which is a continuation of 08/019,550, filed Feb. 19, 1993, now abandoned, which is a continuation-in-part of U.S. patent application Ser. No. 07/843,374, filed Feb. 27, 1992, now abandoned, which is a continuation-in-part of U.S. patent application Ser. No. 07/475,657, filed Feb. 6, 1990, now abandoned, and a continuation-in-part of U.S. patent application Ser. No. 07/305,315, filed Feb. 6, 1989, now U.S. Pat. No. 5,098,426, the full disclosures of which are incorporated herein by reference.

BACKGROUND OF THE INVENTION

This invention relates to tracking systems for aiming a laser beam and/or positioning projected light patterns at a known relation onto moving targets. In particular, the invention is concerned with the detection of, measuring of and compensating transverse movements of optical targets such as an eye during ophthalmic laser surgery as well as non-surgical diagnostic procedures. The present invention is particularly powerful when taken in conjunction with a method for capturing, measuring and compensating for movements along the axial direction such as disclosed by Wm. D. Fountain in U.S. Pat. No. 5,162,642 which is assigned to the same party as the present invention.

Methods of integration of a lateral tracker with depth ranging techniques were disclosed in copending patent application Ser. No. 843,374, entitled "Automated Laser Workstation for High. Precision Surgical and Industrial Interventions", which was filed on Feb. 27, 1992, and which is incorporated herein by reference. In that disclosure, fully automated means to acquire and track randomly moving targets in three dimensions were described, along with methods for interfacing the acquisition and tracking means with a beam aiming and targeting sub-system and a target viewing subsystem, all of which are elements of a complete laser workstation. It is noteworthy that the system and method of said patent application also included, in an alternate embodiment, the capability to distinguish between translational and rotational movements of the eye as an integral part of the full three dimensional tracker.

By comparison with the two earlier disclosures cited above, the present invention emphasizes those aspects and specific embodiments of a transverse 2D tracker that are most critical in allowing a laser beam or projected light patterns to be correlated with and/or directed to a specific location on the target regardless of its lateral movement. Since the application to eye surgery places the most stringent requirements on the tracker, the present invention is described mostly in reference to this application. However, it is to be understood that the invention is broadly applicable to any situation involving precision diagnostic measurements and/or laser operations on moving targets, including industrial applications, such as in semiconductor processing where laser annealing and other techniques call for precise alignment of a mask onto a substrate in the presence of vibrations.

In ophthalmic surgery, the ability to optically track or follow the movement of the patient's tissue—not only the voluntary movements which can be damped with specialized treatment, but also the involuntary movements which are more difficult to control on a living specimen—is recognized as a highly desirable element in laser delivery systems designed to effect precision surgery in delicate ocular tissue. According to Adler's Physiology of the Eye, even when the patient is holding "steady" fixation on a visual target, eye movement still occurs. Such involuntary motion compromises the efficacy of certain ocular surgical procedures requiring great precision. This is true even with total immobilization of the eye, which is not fully effective in suppressing involuntary eye motion while being rather uncomfortable for the patient. Implementation of automatic tracking by remote means would therefore alleviate the need for such immobilization, while offering a method for more effectively accommodating all types of eye motion. Thus, augumenting surgery with on-line eye tracking option can improve significantly upon the accuracy and speed with which old surgical procedures could now be performed as well as enabling new procedures to be carried out for the first time.

In ophthalmology, it is also often desirable to image the tissue simultaneousely with positioning the treatment beam. Effective utilization of an imaging system capable of freezing on a display images or data relating to the configuration of the target during laser treatment requires that the target area be stabilized with respect to both imaging and the laser focal region, thus enhancing the accuracy of energy deposition in tandem with viewing sharpness. The ability to stabilize a video image of a moving target during the surgery procedure itself is especially desirable in those high precision laser interventions employing an instantaneous full image rather than a series of scanned images, such as described in co-pending U.S. patent application Ser. No. 843,374, which is incorporated herein by reference, and in U.S. Pat. No. 5,098,426.

In still other applications relating to diagnostics of targets, tracking can serve an important function in allowing cross-registration of successive readings taken across a moving target. By correlating the true positions of given target segments at the time the readings are taken, the effects of target motion can be compensated for via programming in the computer (i.e., software). In application to corneal surface mapping, utilization of transverse tracking, especially in concert with a depth tracking method that can keep the distance to the eye constant, e.g., as was disclosed in co-pending U.S. patent application Ser. No. 945,207, opens up the prospect of performing true point-by-point thickness and curvature measurements with standard scanning techniques. For example, by aligning separate readings relative to each other, accurate reconstruction of both anterior and posterior surfaces of ocular tissue such as the cornea or the lens can be feasible by scanning the eye with just a slit illuminator coupled to a CCD camera to detect each surface's reflections. Using such simple instrumentation to perform simultaneous surface and thickness measurements was not possible prior to this invention.

Prior attempts to derive simultaneous pachymetry and topography information such as by D. J. Gormley et. al. in *Cornea*, vol. 7, pp. 30–35, 1988 using a scanning laser slit lamp and a photokeratoscope were clearly hindered, among other factors, by the lack of cross-referencing that only tracking can provide. Thus, to compensate for eye movement, each slit lamp image reading consisted of an average of a series of measurements, a procedure which could take up to several minutes. To map the entire cornea in this manner would then clearly require an inordinately long time, especially since, to maintain a common reference point between successive readings, the patient would have to stay fixated throughout the entire scan. By adding means for on-line tracking, the number of required readings can be significantly reduced to where a combined method of depth and surface profiling becomes practical, even allowing the possibility of utilizing a slit illuminator alone for both measurments.

In general, stabilization of a moving target requires defining the target, characterizing the motion of the target, and readjusting the aim of the optical system repeatedly in a closed-loop fashion. For ophthalmic surgery, requirements for a tracking system are set by the type of eye motion, which fall into three categories: microsaccades, drift and high frequency tremor. The high frequency tremors, of about 90 Hz set an upper limit to the frequency, but are of a very small amplitude (up to 40 seconds of arc). Microsaccades are highly accelerated motions with constantly changing directions but lower frequencies (a few Hz). These small but rapid eye movements, combined with slow drift (about 1 minute arc/sec), prevent the retinal image from fading. Analysis of measurements of peak velocity-magnitude-duration parameters by e.g., A. Terry Bahill et al. in *Invest. Ohthalmol. Vis. Sci.*, Vol. 21, pp. 116–125, 1981, indicate that requirements set for lateral eye tracking should include, as a goal, the ability to respond to movement with accelerations of up to 40,000 deg/sec$^2$. This translates to amplitudes of about 1 degree at maximum frequencies of 100 Hz and increasing to nearly 15 degree at 20 Hz. Meeting these response goals while maintaining accuracies on the order of 5–10 microns (as may well be desired in certain ocular surgical interventions near the visual zone), means that any moving parts within the tracker apparatus must not contribute internal vibrations, overshoots, or other sources of positioning error which could cumulate to an error in excess of the prescribed micropositioning tolerances. Other applications may impose tighter requirements on some parameters while relaxing others, depending on the margins of error set for a given process or procedure and the required overall system performance. We do expect, for example, that compensation over larger amplitudes and/or at higher frequencies may be desired in certain micromachining applications, which tighter requirements may, however, be offset by the ability to mark the workpiece to produce sharper tracking landmarks. Such target signal enhancements are not possible for ocular tissue without invading the organ itself, which is what makes the eye tracking application so uniquely demanding.

To date, no instrument has succeeded in tracking the human cornea in a cost effective manner. Previous attempts at achieving this result fall into one of two distinct categories, namely optical point trackers and correlation trackers, the latter including numerous variations of pattern recognition and edge detection methods. Optical point trackers utilize various lens-like properties of the eye to locate optically distinguished locations such as the first, second, third and fourth Purkinje points. For example, Crane and Steele (*Applied Optics*, Vol. 24, pp. 527, 1985) describe a dual Purkinje projection technique to compare the displacement of two different-order Purkinje projections over time, and a repositioning apparatus to adjust the isometric transformation corresponding to the motion. Similar application of dual Purkinje technique to a stabilized visual system was advanced by Crane (U.S. Pat. No. 4,443,075) using a fundus illumination and monitoring device. These and similar Purkinje image-based tracking methods purport to follow the movement of the anterior surface of the eye. While such techniques possess, in principle, sufficient speed to follow the displacement of Purkinje points, they do include an implicit assumption that the eye moves as a rigid body. In reality, however, the eye does not move as a rigid body, hence localization of the Purkinje points can be influenced by transient relative motions between the various optical elements of the eye, which leads to fictitious position information for identifying the surface of the cornea. In addition, such systems are rather complex and tend to exhibit large interperson variability in their calibration setting, which requires continuous real-time adjustments of the amplitude of the controlling signals.

The other class of tracking methods suggested in prior art involve, in one form or another, digital correlation techniques. These include retinal image trackers and various pattern recognition algorithms involving edge detection techniques. In either case, very fast frame-rate CCD cameras and sophisticated processing algorithms are required along with fast servo-controlled mirrors closing the loop. This is because, in general, methods based on pattern recognition are fundamentally digital, requiring high frequency updates. With the frequency response limited in practice to about one tenth the update frequency, digital signal comparisons are considered to be relatively slow. In the case of tracking eye motions, setting the sampling frequency to about an order of magnitude higher than the highest frequecy to be pursued translates into. kHz rates, leaving less than one thousandth of a second for processing the signal information.

Several other practical difficulties plague most pattern recognition techniques including the need for rather prominent and recognizable features, which are not easily located in any of the eye's structures. Also, techniques predicated upon high speed correlation processing of video signals are often deficient due to unfavorable trade-offs between field of view and spatial resolution. Specifically, since the image processing algorithms are limited by the size and spacing of the view elements (pixels), the digital methods do not afford continuous resolution. Increasing the resolution exacts penalties in terms of the field of view. Yet, relatively large areas must be acquired or else a beam must be scanned. Consequently, the system is either light starved in the former case or else requires extremely regular and fast moving optical deflectors in the latter, along with complex electronic processing which can further limit the already slow response time of the system.

While there have been some claims of successful tracking for the retina (see for example, Milbocker and Feke in *Applied Optics*. Vol. 31, pp. 3719–3729, 1992, Katz et al. in *American Journal of Ophthalmology*, vol. 107, pp. 356–360, 1989 and A. Forster in *Proc. of Ophthalm. Tech.*, SPIE vol. 1423, pp. 103–104, 1991), to our knowledge no instrument of this type has produced a real-time stabilized image of the cornea to date. Typically, CCD cameras are used to analyze the translations of an image on the retina from which the resulting coordinate transformation could be computed. The data is then fed to e.g., galvanometric driven mirrors which are repositioned so as to maintain a beam at the selected location of the subject. Other than the issues alluded to above regarding inherent limitations of digital edge detection techniques, the need in most of these instruments to utilize galvanometer drives to reposition mirrors at nominal kHz acquisition rates adds complexity to the system while further limiting the positioning accuracy due to overshoot problems.

Bille et al. (U.S. Pat. 4,848,340) describe a simpler variant on the pattern recognition method, whereby a grid is marked, using a laser, on the epithelial surface of the cornea, in a known reference alignment to the eye's visual axis. An infrared optical system monitors reflections there-from, generating an error signal whenever the position of the mark deviates from reference alignment. The error signal is transmitted to a laser guidance system containing a fine tuner (consisting, e.g., of one or more galvanometrically controlled mirrors) which steers the laser beam in a manner that reduces the error signal to null. This type of a tracking system requires a sensor such as a photodiode array that can detect variations in the intensity of the reflected light pattern to generate signals representative of grid movements. These sensors suffer from both slow response times and limited spatial resolutions. Typically, with accuracy bounds set by the space between the array elements divided by the magnification, it is difficult to obtain resolutions better than 50 microns or so in practical systems. Furthermore, like any closed-loop feedback control that requires comparison of input signals to some reference, the technique taught by Bille et al. is digital in nature, which means that it suffers from similar drawbacks as image trackers and edge detectors in general, including processing speeds limited by the servo rate to less than a millisecond.

It should also be appreciated that a target tracking and laser positioning mechanism that relies on a mark on the surface of the cornea in order to perform corneal surgery, such as described by Bille's tracking method, might lead to misdirected positioning of laser lesions below the surface when combined with any suitable focused laser. Thus, the mark would change its absolute location due to changes in the structure and shape of the material being modified that are caused by use of a laser surgery instrument itself, rather than by eye motions. It is therefore not clear that a tracking method based on marking the target tissue itself is compatible with laser surgical interventions performed simultaneously with the tracking. Moreover, one of the features of the present invention is to enable non-incisive procedures inside target tissues by remote means. It would hence be counterproductive to mark the surface of the cornea for the sole purpose of following the motion of said mark.

In another embodiment of Bille et al. U.S. Pat. No. 4,848,340, the tracking is based on a reference provided by an empirically determined offset between the eye's symmetry axis and the eye's visual axis. It is claimed that tissue can be tracked by monitoring the reflection from the apex of the cornea, thus avoiding the need to mark the eye, and/or, rely solely on patient fixation. However, with this technique, the tracking does not follow tissue features generally corresponding to the targeted surgical site itself. Instead, Bille et al.'s technique tracks reference points that are, like Purkinje points, a property of the optical system and do not correspond to any particular physiological tissue. They are therefore separate, remote from and may be unrelated to the targeted surgical site. The accuracy of the tracking is thus compromised in direct proportion to the degree of the reference points' remoteness relative to the surgical site, while ambiguities inherent in measurements of the symmetry and/or the visual axis will further reduce the accuracy with which positional changes of the targeted surgical site can be pursued using these methods.

By contrast with either pattern recognition based systems or optical point trackers, the methods of the present invention disclosed herein involve contrast tracking which does not rely on well-defined edges and/or patterns that must be compared to some reference. This allows great flexibility in selecting the tracking landmark, since prominent and constant edges are not required for acceptable signal-to-noise ratios. In the preferred embodiment, the tracking information is to be obtained through means contiguous to the target region, which is mechanically and structurally considered as part of it, but is unlikely to be affected by the course of the laser intervention. For example, the system and techniques disclosed herein resolve, for the first time, difficulties associated with previous attempts at limbus tracking. The limbus, located at the outer edge of the cornea, presents several advantages as a tracking landmark for corneal procedures. It is actual tissue that is contiguous to the targeted corneal tissue and is expected to provide a faithful representation of non-surgically induced displacements. Yet it is located far enough from the site of operations so that the transient displacements occasioned by the impact of the laser pulse on the target site will be damped sufficiently to avoid inducing fictitious tracking signals. Prior limbus trackers have not been successful because the limbus is a poor candidate for any technique relying on edge detection, constituting not a sharp boundary but a transition zone between the cornea and the sclera. Therefore, poorly defined edges and shapes that appear to deform due to rotations have led to difficulties in extracting signals out of noise.

The present invention overcomes these shortcomings because it is practical even in the absence of prominent, well-defined or even temporally constant edges. The only two requirements are that sufficient contrast be present, and that the feature possess a degree of symmetry. In the eye, these conditions are fulfilled by e.g., the limbus structure and in most cases, the pupil as well. In our co-pending patent application Ser. No. 843,374, a method for tracking the limbus was disclosed relying on a set of two quadrant detectors as the position sensor. The present patent application expounds on that disclosure by highlighting a unique electronic control system that can be used for the tracking to great advantage, and including as a desirable feature a dual feedback loop that can be all analog, thus significantly increasing the practical speed of operations over comparable digital methods. Along with the added emphasis on the electronic means for realizing rapid limbus tracking, the simplified signal processing and fast logic operations involved in the electronic servo loops of the present invention also allow a substantial expansion of the scope of the previously disclosed limbus tracking method to include other contrast-based tracking landmarks and alternative position sensing detectors as may be needed to implement tracking in different surgical, diagnostic or industrial settings.

SUMMARY OF THE INVENTION

Thus, it is an object of the present invention to provide means for stabilizing the lateral motion of randomly moving targets, allowing an imaging system, diagnostics illumination, and/or laser beam to maintain a lock on the target area, regardless of its movement.

It is further an object of the present invention to provide a means for recording eye movements in real time and in which data can be stored and manipulated for the purpose of compensating for lateral target motion by either hardware or software means.

It is a more specific objective to provide within the tracking system a means for sensing contrast in recognizable large scale boundaries such as the change between the cornea/sclera interface (limbus), thereby to determine the absolute location and orientation of these boundaries, all without having to resort to digital sampling techniques.

It is yet another object to identify the target's velocity vector with sufficient speed and accuracy to be able to guide positioning optics, such as a pivoting mirror, to pursue and compensate target motions in a plane. (also referred to herein as the X-Y plane) perpendicular to the optical (Z) axis of the system as defined, most often, by a final objective lens assembly. The moveable optical element is under the directional control of a rapid servo device.

Still another specific object of the invention is to enable, in a preferred embodiment, all analog execution of electronic servo functions, if desired, including those that provide directional control of the moving optical element, thus circumventing difficulties associated with the slower all-digital closed loop servo systems.

Consistent with these objects, an embodiment of the present invention is herein disclosed, comprising a method and apparatus for precise lateral target tracking useful to ocular surgery and ophthalmic diagnostics, as well as to several other medical and industrial procedures. The techniques disclosed are particularly powerful in combination with an axial (Z) tracking system, such as the modified confocal microscopy-based technique disclosed by Wm. D. Fountain in U.S. Pat. No. 5,162,642 and in U.S. patent application Ser. No. 945,207. The Z-tracker discussed therein is fully compatible with the present system with which it can interface by way of suitable coupling optics and/or the tracking optical element itself, provided that the objective lens assembly is inserted as the first element in front of the target. The present invention also contains provisions, such as additional coupling optics, for interfacing the X-Y tracker with any number of other optical subsystems including, but not limited to, imaging means, laser targeting and treatment means and topography means. Such interfaces and the computerized methods required to implement them in practice, were described in co-pending U.S. patent application Ser. No. 843,374, which is incorporated herein by reference.

In application to laser surgery, tracking by following the subject eye tissue, i.e., recognizing new locations of the same tissue and readjusting a movable element that is optically connected to a surgical laser, assures that the laser will aim at the new correct target location and not deviate from a pre-programmed pattern an unacceptable distance. By also taking advantage of the coupling optics provided within the present apparatus to interface with a viewing assembly, such as a zoom microscope, the tracking system of this invention fulfills an important dual-use purpose: it can greatly enhance the precision of lesion placement in targets as well as improve safety margins by allowing simultaneous presentation of a stationary view (e.g., in the form of continuousely updated video image) of a given section of tissue on a display monitor. It is anticipated that the availability of fast and reliable tissue diagnostics simultaneousely with the surgery itself will be especially valuable in the specific case of ocular surgery (and concerning, in particular, corneal procedures), where obviating the need for eye immobilization, and all the drawbacks thereof, is a much desired feature.

In application to topographic and other diagnostic measurements, the transverse tracker of this invention can be operated in a manner allowing determination of target movement relative to a given coordinate system which is in a known reference to, e.g., the optical axis of the apparatus. Such movement can then be compensated for by software means using programming in the computer. The ability to actually compute and store information concerning target movement in a meaningful way is a valuable tool whenever sequential series of measurements are to be performed by way of e.g., scanning the target while it is moving, so that the results can be extrapolated to reveal a global feature of said target. Such an approach can be profitably applied to topographic and pachymetric measurements aimed at reconstructing, on a point-by-point basis, the curvature, shape and/or thickness of intra-ocular structures such as the cornea and the lens. Providing enhanced cross-registration of adjacent target segments, each referenced to the actual location of the target area at the time the reading is taken, promises to extend surface mapping accuracies to well beyond any existing corneal modeling systems. Furthermore, by interfacing the tracker with other existing instrumentation such as slit lamps and cameras, a host of new possibilities opens up for cross-correlating various optical target properties across wider areas and with higher local accuracies than was demonstrated with any prior art methods.

In application to industrial operations, the system and methods of the present invention can be used successfully to suppress vibrations in various semiconductor processing applications involving micron and submicron precision levels. Implementation of a tracker to detect and compensate for random enviromental vibrations may alleviate the need for expensive and cumbersome isolation equipment, thus leading to significant reductions in capital outlay costs while improving overall yields. These are desirable objectives in operations ranging from automated inspection and short repair of microchips to photolithography and laser annealing.

Like most servo-based tracking systems, the system and method of the present invention rely on returning an error signal generated by movement of the target to zero. However, this is where similarities to other tracking methods end. The key novel feature embodied within the present invention which distinguishes it from prior art concerns an approach to generating tracking signals by way of detecting variations in target contrast, thereby avoiding the need for complex edge detection algorithms. Consequently, position sensing detectors with continuous resolution elements can be utilized, thus eliminating information gaps while avoiding the need for high update frequencies. Also, the electronic control system is compatible with fast, simple, all-analog techniques for processing the signals from position sensing detectors and/or transducers and translating them into command signals for a servo control mechanism. Such an analog option is not feasible with other tracking methods based on digital data acquisition systems.

The tracking system is at least comprised of an illumination source, a sensor, a moveable optical element, such as a mirror, a two-dimensional logic board, and a dedicated microprocessor or logic board including appropriate signal processing firmware and software. Interfaces with other system elements such as laser aiming, target viewing and/or depth ranging subsystems may all be included as part of the optical train, while suitable control ports provide electronic interface with these other functions as well as with a central computer (using A/D converters where required). The transverse tracker disclosed herein is thus best considered as a module ready to be integrated with other system functions, be they diagnostic or therapeutic in nature.

In a preferred embodiment of the invention, the illumination light is projected off-axis relative to the optical axis of the instrument so as to minimize interference from either the treatment light (typically an intense laser beam) or depth ranging light (which can also be a laser, such as a low power HeNe). This configuration leaves considerable flexibility as to the choice of the tracking light source and may include lamps, LED's and laser diodes, depending on the reflectivity properties of the tracking landmark used and the overall application needs. The position sensors are also selectable from among a class of position-sensiing photodetectors, all possessing fast response times (of well below a tenth of a millisecond) and excellent resolutions (on the order of 1 micron), with a view towards optimizing a given system performance. In one preferred embodiment of the invention, the transverse X-Y tracking detector consists of a set of two high speed quadrant detectors which provide an ideal match to tracking the limbus of the eye. Alternative detectors, including lateral-effect and superlinear position sensors, may however be selected for eye tracking or other applications, without compromising the effectiveness of the present invention.

An X-Y logic board comprises a key element of the electronic processing serving as the central "switchboard" of the servo tracking loop. This is where voltage signals from the detectors corresponding to target motion are received and converted to appropriate commands for controlling the tracking optical element assembly drivers so as to compensate for said target motion by repositioning an movable optical element, such as a mirror. Since analog control signals can be used, processing speeds are not a limiting factor, even for applications requiring high repetition rate (>1 kHz) lasers. Thus, laser firing can always be disabled, if necessary.

In alternative embodiments, either piezoelectric, electromagnetic or galvanometric drives can be used to steer the moveable system element, such as a mirror to drive the error signal generated by target motion back to null. This component must however be capable of moving with sufficiently high acceleration and velocity to compensate for the fastest motion possible by the intended target. Since the operation of the system is not limited by either the processing speed of the servo loops or the detectors' response time, the driven optical element with its finite moment of inertia is likely to provide the main limitation on the extent and rate of motion which can be compensated, so considerable care must be exercised in selecting the type of drive to match a given application needs. Nonetheless, the manner of operation and the principles of the present invention do not depend on specific drive mechanis, a particular transducer, or the moveable optical element, all of which components can therefore be selected to match the needs of specific applications.

Intrinsic to the tracking scheme disclosed herein is the choice of a suitable tracking landmark possessing of sufficient contrast under illumination by the light source used. This is a relatively easy condition to fulfill, lending the system considerable flexibility with regard to said choice. Ideally, the tracking landmark would be located contiguous and in proximity to the targeted tissue, yet without being coincident with the precise target site itself, since this site will change during the course of the intervention. For one preferred embodiment involving corneal procedures such as refractive surgery, the eye limbus at the rim of the cornea provides sufficient contrast to serve as the tracking landmark for procedures affecting either the central or peripheral portions of the cornea. Alternative landmarks such as the pupil, which may be useful when procedures in zones peripheral to the visual axis are contemplated, also fall under the domain of this invention. For still other, non-surgical interventions, a suitable feature can usually be artificially impressed upon the workpiece in sufficient proximity to the target site and with enough contrast to allow the efficatious employment of the tracking methods discussed in this invention.

It has been determined that target motions with accelerations of up to 40,000 deg/sec$^2$, corresponding to rates of over 100 Hz for amplitudes of nearly 1 mm along two axes (or larger amplitudes but at lower rates), at accuracies of 5–10 microns can be pursued with the described embodiments of the invention, which should more than adequately compensate for all types of involuntary eye motion. Such speed and precision were not attainable in a predictable, systematic manner with any of the prior instruments or practices used.

The novel features of this invention, both as to its structure and method of operation, along with further objects and advantages thereof, will be apparent from the following description of preferred embodiments, considered along with the accompanying drawings.

BRIEF DESCRIPTION OF THE DRAWINGS

In FIG. 1 the tracker is configured for tracking an arbitrary landmark, shown for illustration purposes as a circle.

DESCRIPTION OF PREFERRED EMBODIMENTS

Figure 1:
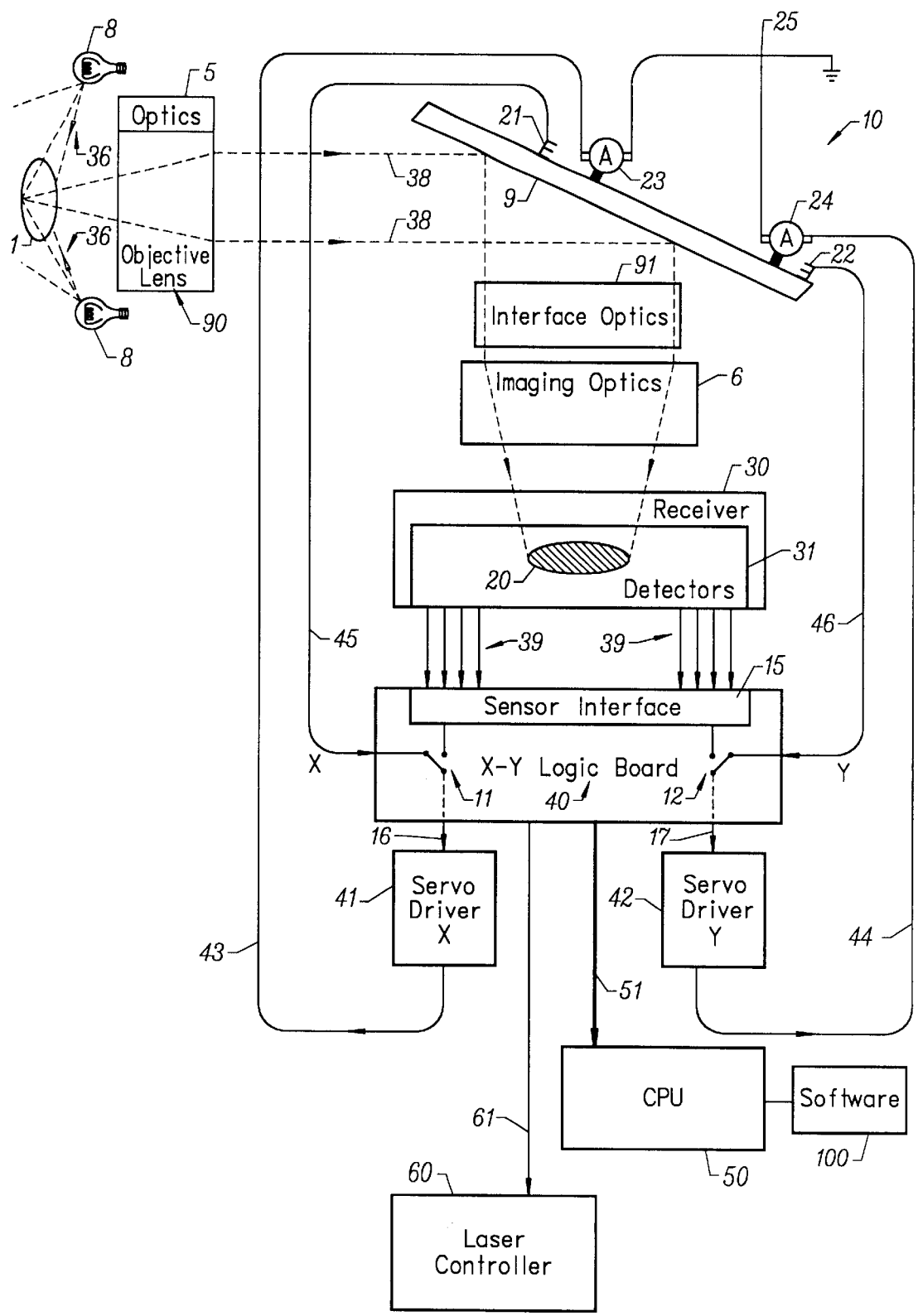
FIG. 1 is a schematic block diagram of the transverse tracker, its associated optical and electronic elements, and the information flow, electronic feedback control paths and servo loops.
Figure 2:
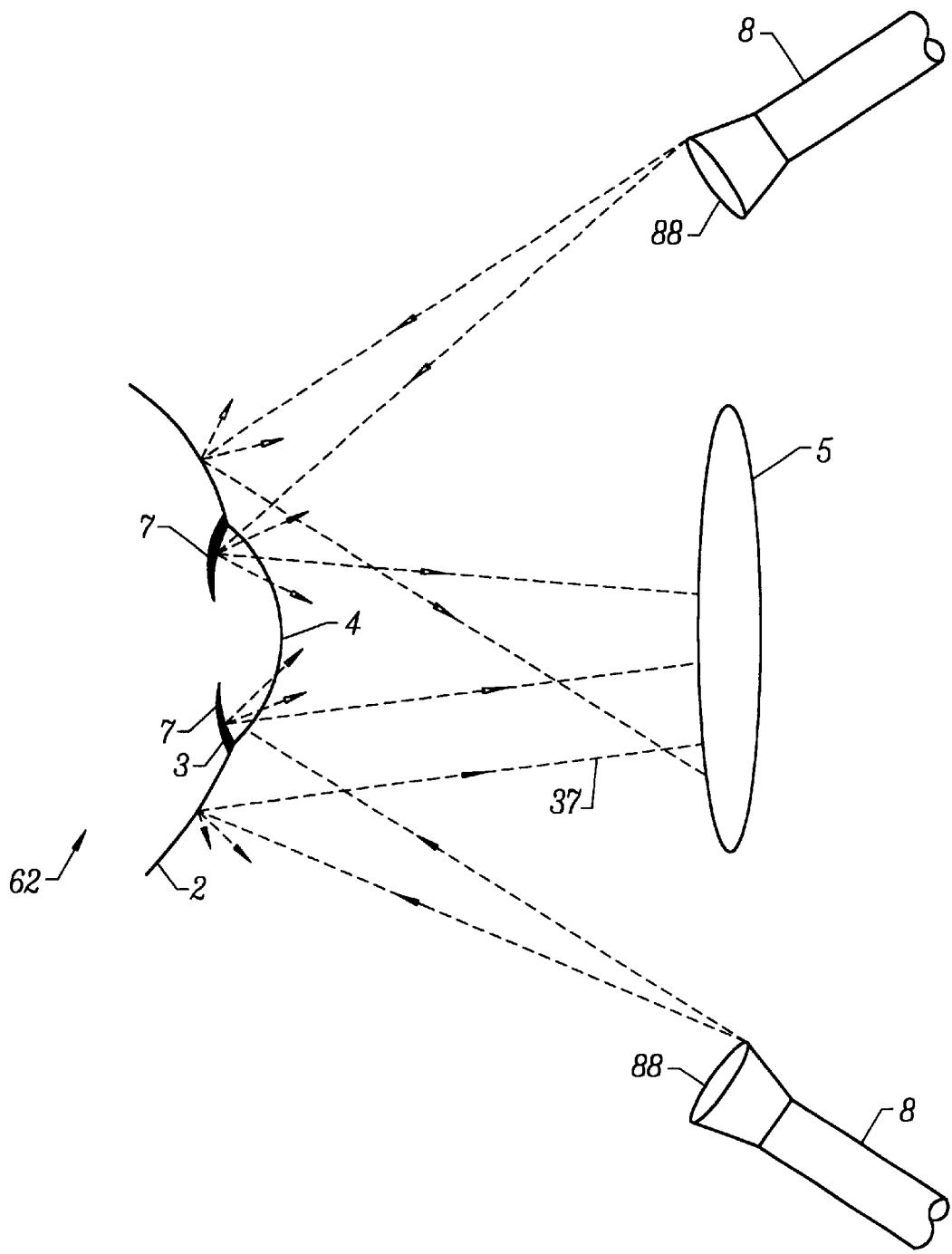
FIG. 2 is a schematic elevation of an example of incident and reflected light rays for an illumination system corresponding to a preferred embodiment of the invention in which the limbus of the eye provides the tracking landmark. Attention is drawn to the fact that the scattered component of the reflected light is selected for defining target contrast.

FIG. 1 is a schematic of a preferred embodiment of the transverse tracking assembly 10, shown here as tracking a symmetrical landmark 1 belonging to an arbitrary moving target. For illustration purposes, FIG. 2 shows the specific target consisting of an eye 62 using the limbus 3 as a tracking landmark, which situation pertains to certain ophthalmic surgery and diagnostics procedures. While ophthalmic interventions comprise one primary application that falls under the domain of the present invention, it to is to be understood that the target tracking system disclosed herein encompasses other types of medical diagnostic and surgical procedures as well as non-medical and industrial operations, involving high precision operations on objects subject to random movement.

Referring initially to FIG. 1, it will be seen that the system 10 employs an optical train consisting at least of illumination source(s) 8, system optics 5 including, preferably, an objective lens assembly 90 defining the axial (Z) direction, a movable system element 9, imaging optics 6, and a receiver assembly 30 which includes detectors 31. The optics designated 91 are optional and may include further components to permit interfacing the tracking system to other assemblies such as an axial tracker, a target viewing means, a treatment laser aiming system and others, as dictated by particular application needs. The electronic subsystem also shown in FIG. 1 consists of electric signals 39 from the sensors 31, an X-Y logic board 40 controlled (line 51) by a central processing unit (CPU) 50 which includes system software 100 to aid in the interface to other assemblies, X and Y servo drivers 41, 42, and the associated relay paths 43 and 44 to actuators 23 and 24 that control orientation of the moving element assembly 9 along its respective X and Y axes. In a preferred embodiment applicable to laser interventions, there is also a link 61 between the logic board and a laser controller 60 whereby commands to enable or disable laser firing are transmitted. As will be discussed below, a critical function in the electronic operation of the system is served by transducers 21 and 22 contained within the moving element assembly 9 and linked (via control lines 45 and 46) with switches 11 and 12 shown as part of the logic board 40.

In a preferred embodiment, the optical portion of the tracking path shown in FIG. 1 comprises several steps. Light 36 from the illuminators 8 is projected onto the target, reflected from the tracking landmark 1, passes through the system optics 5 which may include an objective lens 90 acting to collect and collimate the light along path 38, whereupon it impinges upon the moving system element 9, shown here as a reflecting surface that may be part of, e.g., an X-Y tracking mirror (it could be a lens). The light is then propagated via interface optics 91 to imaging optics 6 which focus the light onto detectors 31 contained in the receiver assembly 30. Generally, a lune-shaped pattern 20 is projected in this manner, consisting of a bright field corresponding to one side of the tracking boundary adjacent to a darker field representing scattered light from the other side thereof, which together represent the target contrast. The sensors 31 may consist of one or several coupled detectors, preferably with a continuous detecting surface, and arranged so as to produce voltage change information 39 in response to variations in the position of the illumination centroids. As the target moves, so does the high contrast boundary, thereby altering the signal(s) produced by various parts of the sensor(s), as will be apparent from subsequent discussion accompanying specific embodiments of the sensors (per FIGS. 6 and 7 below).

In one preferred embodiment, the transverse tracker of the present invention is intended for use with an ophthalmic laser surgery instrument, as was disclosed in co-pending U.S. patent application Ser. No. 843,347 and which is incorporated herein by reference. In accordance with this application, the eye must be tracked without incurring undue interference from a bright treatment laser, which is simultaneously on-line with the tracker. As shown schematically in FIG. 2, off-axis illumination source(s) 8 may be utilized in this case, with said sources consisting of, e.g., a bright lamp (such as tungsten) coupled to fiber optics bundle and projected through lens(es) 88 onto the general region of the cornea 4 of eye 62. Light scattered from the iris 7 and the sclera 2 and generally represented by ray 37 (corresponding to the scattered light component of the reflection) is collected by the system optics 5 and propagated on as was discussed in connection with FIG. 1 above. In this preferred embodiment, the limbus 3, at the outer rim of the iris, comprises the boundary used as the tracking landmark. The advantages of tracking the limbus for procedures targeting the anterior segment of the eye will become more evident from subsequent discussion. There are other cases and procedures, both surgical and diagnostic, for which the pupil of the eye may advantageously serve as an alternative landmark possessing sufficiently high contrast. In still other, alternate embodiments of the invention, tracking certain retinal features may also fall within the domain of the tracking system disclosed herein, without compromising the principles and methods involved in its operation.

Referring back to FIG. 1, it will be appreciated that conversion of the light pattern to electric signals effectively constitutes handover from the optical to the electronic subsystem. Once produced, the voltage information is relayed to the X-Y logic board 40, which serves as the central "switchboard" of the electronic tracking loop. Functionally, the board can quantify and correlate target movement with intensity changes at the detector; compute the required displacements of the moving element, such as a mirror, necessary to compensate for said motion; effect the appropriate analog control signals to the moving element control assembly; and issue digital commands to a laser firing controller, following analog to digital (A/D) conversion where applicable. The board is where the X-Y coordinate shifts (magnitude and direction) are first computed from the voltage signals produced by the sensor, based on formulas applicable to specific detectors that are contained within the sensors interface 15. Preferably using embedded firmware, the board converts these coordinate values into mirror angular corrections which are relayed to servo drivers 41 and 42 via control lines 16 and 17, respectively (via switches 11 and 12 in a different position from what is shown in FIG. 1, as will be apparent from further discussion below). The servo drivers activate, in turn, actuators 23 and 24 by way of control signals 43 and 44, which causes the X-Y mirror assembly to pivot about its axes, thus effectively changing its orientation to pursue the motion of the target, and stabilizing it with respect to system 10. To close the electronics loop, the X-Y logic board contains two switches 11 and 12 relating to X and Y displacements respectively. These switches allow interchanging of the servo driver connections between transducers 21 and 22 and detector signals 39, representing the two modes of operation inherent to the functioning of the two-dimensional tracker that is the subject of this disclosure, as discussed further below.

The two transducers 21 and 22 are also labeled X and Y, corresponding to the two orthogonal axes lying in the plane perpendicular to the optical axis. These position sensing elements fulfill an important dual function in the operation of system 10 by allowing the moving element 9 to either stabilize in the absence of a target, or to calibrate the actual magnitude and direction of the moving element's displacements, and therefore the target's (this latter situation being applicable to diagnostic measurements as will be elaborated further below). Generally, the 40 transducers form an integral part of the moving element assembly 9, hence they represent target displacement vectors relative to that frame of reference. In one preferred embodiment, each transducer consists of a simple "flag" —a low-cost type of position sensor consisting of a moving bar and a sensor, whereby angular displacements can be controlled and measured in a purely analog fashion, without the need for any convert commands or wait loops. In alternative embodiments, digital converters such as resolvers and Linear-Variable-Displacement-Transducers (LVDT) can also serve as transducers, if desired, with only minor modifications in the operation of system 10.

Figure 3:
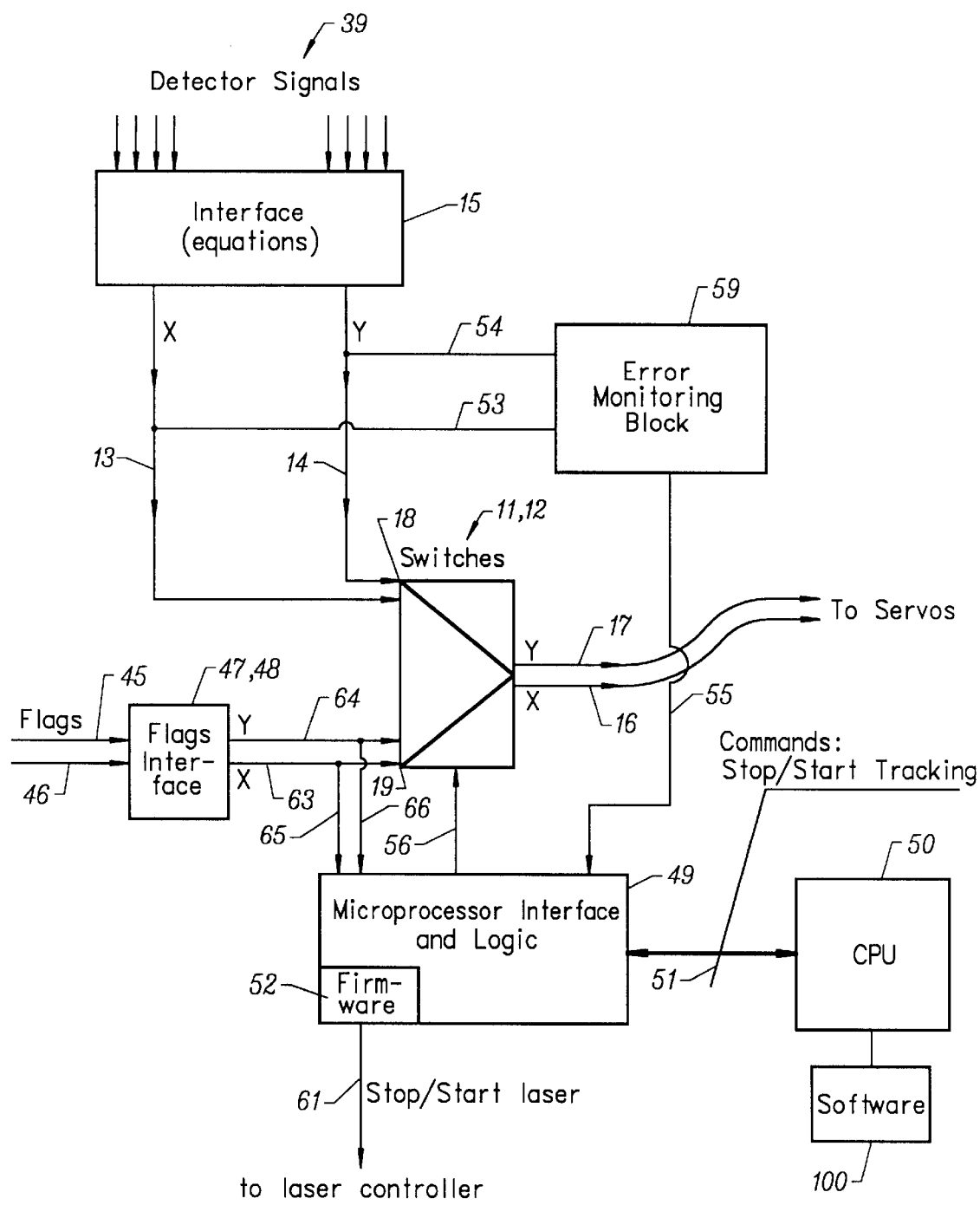
FIG. 3 is a schematic block diagram illustrating in more detail the key functions and components of the X-Y logic board in relation to the various interdependent electronic control loops as well as devices considered external to the tracker, such as the CPU and a laser controller.

FIG. 3 shows a more detailed view of the X-Y logic board schematics. For ease of illustration, only one switch is shown in the center of the figure, representing both X and Y switch functions 11 and 12, as these two always work in tandem. Also, the transducers, which, for simplicity, are labeled as "flags" in FIG. 3, are, in fact, to be understood as comprising any one of the general class of devices discussed above, and designated 21 and 22 in FIG. 1.

The two positions of the switches 11 and 12 labeled 18 and 19 in FIG. 3, depict the two modes of operation of the system 10. In one mode of operation ("tracking mode") the switches are set to position 18 ("closed"), whereupon the X and Y signals 13 and 14 representing new target positions are fed through the switches to X and Y servo drivers by way of control lines 16 and 17, thus activating the tracking feature. Cross-referencing with FIG. 1 above, it will be recalled that the servo drivers subsequently instruct the actuators (or servo motors) 23, 24 of the moving element 9 to position the change (via control lines 43 and 44 in FIG. 1) in a manner that returns the X-Y signals to zero (i.e., upon the next check review, no deviation from nominal position is detected). From this description it should therefore be appreciated that the sensor interface 15 serves effectively as an analog "comparator", generating the two error signals (equivalent to X and Y signals) used as input to the servo drivers when the switches are in position 18, and reflecting the difference between the actual position of the target and a reference nominal position. To produce these position signals, input is provided to interface 15 in the form of voltage signals 39 which are proportional to the relative positions of light centroids on the detectors, the light being that reflected from the target. Eight voltage signals are indicated in FIG. 3 (and also in FIG. 1) which are grouped in two sets of four, with each set representing one detector. Upon further discussion of specific detector embodiments below, it will be appreciated that such grouping of signals applies to one type of detector configuration (namely, two quadrant detectors) and that other types of sensor arrangements may yield different groupings. In particular, there would be fewer signals if a linear detector were to be used. In either case, the equations used to determine the new target positions are inherently analog, as none of the signals has been digitized up to this point.

Note that when zero X and Y signals are defined in relation to a reference position, it is to be understood that the said position is established upon commencing the tracking procedure as a nominal position. Typically, this reference position is somewhat arbitrary, but can be set to reflect a convenient target orientation. For example, in one preferred embodiment of the present invention relating to ophthalmic procedures, the reference position for the target, in this case the eye, to which all subsequent signals are to be compared, is set by aligning the patient's line of sight with the optical axis of the instrument. Such a position provides a relatively unambiguous determination of a reference point in space that is unique to each patient, as the nominal position of the eye relative to the instrument (i.e., to the position sensing detectors).

Tracking is initiated and stopped upon commands issued by the CPU 50 through control line 51 to a microprocessor interface 49. Firmware 52 embedded within the microprocessor is applied to initialize logic to interact with the CPU and interpret commands from the CPU. Since the CPU 50 comprises, typically, a digital VME based bus, it is understood that provisions are included to issue the start/stop tracking commands in digital format. As indicated in FIG. 3, issuing these commands is the main function of the CPU 50 and its associated software 100 in relation to the operation of the tracker alone; however, when the tracker of the present invention is part of a larger system, the CPU provides also an essential link for interfacing with other assemblies such as an axial tracker or a target viewing system.

FIG. 3 also shows an error monitoring block 59 that is operatively connected via control line 55 to microprocessor interface 49, which, in turn, is seen to also command switches 11 and 12 as represented by relay line 56. Functionally, block 59 monitors (lines 53 and 54) the X,Y signals 13 and 14 and checks them against logic contained within the microprocessor interface. In a preferred embodiment, should the error signals be deemed to be too large or otherwise deviate by unacceptable amount(s) from the prescribed range, thus indicating loss of tracking, or if a stop tracking command was independently issued by the CPU for any reason, the error monitoring block can instruct a laser controller to disable further operations such as laser firing, as indicated by control line 61. This added capability to disrupt laser firing directly through the microprocessor interface 49 and independent of the CPU is regarded as a key safety enhancing feature provided within the tracker electronics.

The second mode of operation illustrated in FIG. 3 is activated when the switches move to position 19 ("open"), thereby shifting system control to the transducers interfaces 47 and 48, through connections 63 and 64. This mode of operation (designated "stand-by mode") was the one depicted in FIG. 1. It generally corresponds to a situation when the target is not recognized as evidenced by the absence of appropriate X and Y signals, or when tracking is stopped upon command by the CPU. With system control shifted to "flags", output signals 16 and 17 issued to the servo drivers instruct the actuators to set the moving element to its default position. Thus, in the absence of a target, the "flags" substitute for tracking signal, as indicated by input signals 63 and 64, channeled through the flags interfaces 47,48 by control signals 45 and 46 that are physically connected to the flags themselves. This feature not only prevents the mirror from random oscillations, but also allows recovery of the tracking if it is momentarily lost through e.g., the blinking of an eye, or some momentary undue enviromental vibration. In particular, it will be appreciated that this mode of operation constitutes a feed back loop, since the microprocessor is instructing, via control line 56, the servo drivers to reorient the moving element back to a default position, and the signals from the flags confirm that this position has, in fact, been attained. Once the default position has been confirmed, the switches 11 and 12 can again "close" (or move back to 18), and normal tracking may be resumed. It is important to realize that even during operation in the normal "tracking mode", the microprocessor interface 49 receives continuous signals from the flags as indicated by control lines 65 and 66, which relate the moving element's absolute position. These signals can provide an additional monitoring function as to the proper functioning of the system and may also constitute one more input data on the basis of which the microprocessor determines whether to continue or interrupt the tracking procedure.

The actual operation of the dual mode control system will be best appreciated by reference to the particular situation involving laser eye surgery where the blinking of the eye is to be accomodated. In accordance with the principles of operation as described above, the motion of the eye lid can be rapidly detected through significant alteration of the relative contrast as perceived by the position sensitive detectors, which results in large error signal (13 and 14). The error monitoring block would then issue a signal 55 to the microprocessor interface. Laser firing can then be immediately interrupted through signals 61 leading directly from block 49. Since the servo drivers simultaneously cause a repositioning of the movable element by amounts exceeding previousely set bounds, this deviation from normal parameter range is also sensed by the flags and transmitted to the microprocessor interface 49 (through 65 and 66). Once alerted, the micrprocessor issues a signal 56 to move the switch to position 19 thus setting tracking to stand-by mode. When it is determined that the error signals have returned to normal magnitude range, tracking and firing can both be re-activated a short time later. The manner in which tracking is resumed most effectively involves returning the moving element to the nominal position recorded just prior to the interruption, corresponding to a particular target contrast relationship stored in the microprocessor memory.

The manner by which the unique elements of the tracking system 10 converge to enhance both the safety and efficacy of even the most delicate surgical procedures or ultra-high precision industrial interventions is now apparent. Thus, as was alluded to above, laser firing can be de-activated whenever tracking is lost and re-activated when the target is recovered, almost instantaneously, thereby greatly increasing both the speed and safety of operations. This feature is particularly useful in accommodating a situation involving momentary interruption of the tracking procedure, such as might occur during the blinking of an eye, in which case the laser firing can be deactivated momentarily without shutting down the operation of the entire system. Incorporation of a simple hardware component such as the flags directly into the electronics loop is therefore seen to represent one particularly innovative aspect of the method and operation of the present invention, by providing a fast and reliable method to interrupt and resume tracking as well as additional monitoring means to enhance system reliability.

Furthermore, once built-in, the function of the flags can be expanded to encompass, in alternative embodiments, still another role. In particular, they may be used to obtain a direct read-out of the moving element's (and hence, target's) positions as an aid to diagnostics of randomly moving targets. In one such alternative embodiment, the voltage signals from the flags are first calibrated against deflection angles of the moving element relative to the pre-determined default position, with the resulting curve stored in the microprocessor interface logic 49. When the system is in the tracking mode, inputs in the form of specific voltage readings from the flags (which are continuously channelled into the microprocessor by way of relay lines 65 and 66) are weighed against the pre-calibrated voltage-to-angle curve, thereby providing a determination of the moving element's rotation angle(s). A subsequent coordinate transformation using an algorithm specific to the optical parameters of the system would then yield the corresponding target motion parameters. This method is thus seen to provide, an effective means of tracking motion through software and can be used to establish any number of target motion parameters, depending on the number of degrees of freedom associated with a given application. This includes, in particular, the possibility of characterizing target motion in three dimensions, provided the information from the two-dimensional lateral tracker of the present invention is combined with data obtained separately from an axial, or depth tracker such as was disclosed by Wm. D. Fountain in U.S. Pat. No. 5,162,642.

Figure 4:
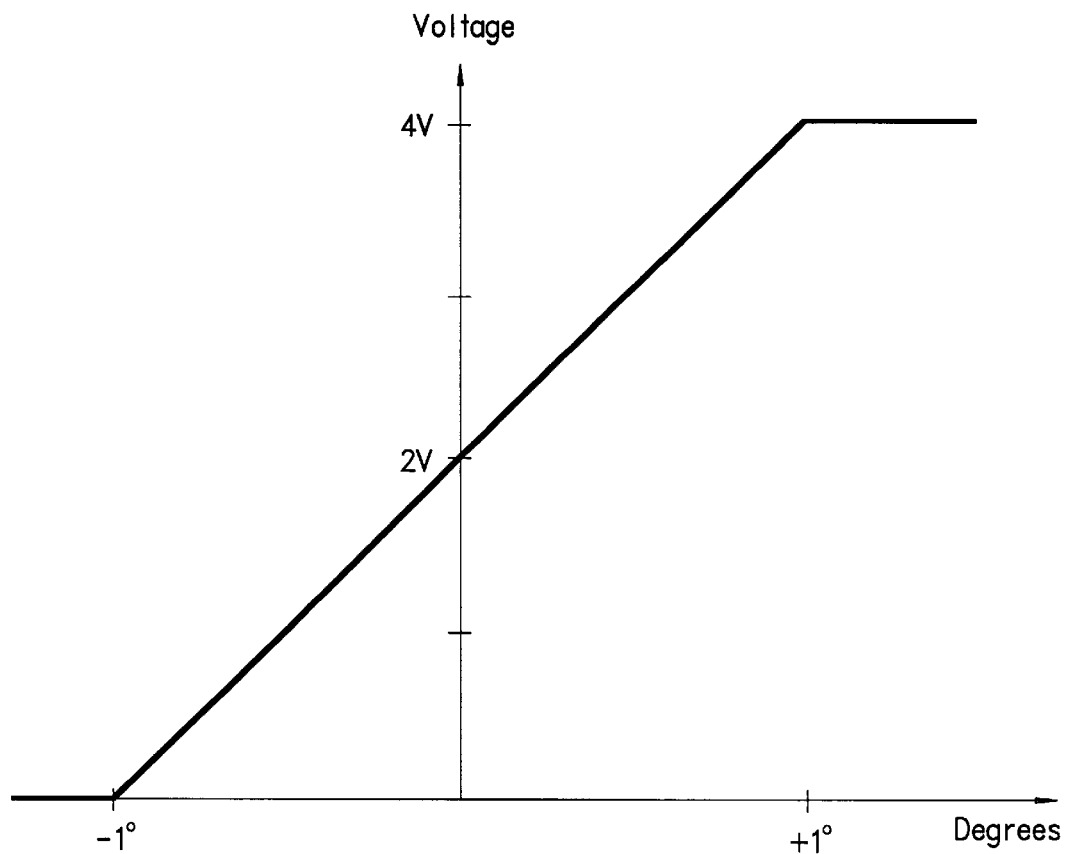
FIG. 4 is a graph depicting, for one axis, an example of transducer voltage dependence on optical element motion, expressed in degrees.

In one preferred embodiment relevant to the eye, the movable optical element comprises a reflecting mirror. Assuming maximum flag voltages of 4–5 volts, an example of a voltage-to-angle calibration curve such as shown in FIG. 4 can be obtained. This situation may be representative of a diagnostic system aimed at acquiring topographic measurements of corneal surfaces, where it has been determined that a range of travel for the mirror of approximately 2 degrees around either axis is adequate to obtain desired local curvature accuracies (ideally better than 10 microns). It is noteworthy that such a parameter range is a practical possibility with an optical system that is compatible with focal lengths In excess of 100 mm (leaving enough clear space to accomodate a scanning slit lamp system, for example) and sufficient depth of focus to acquire both front and back surfaces of the cornea (about 4 mm). From inspection of FIG. 4, it is apparent that since the curve Is linear, a given voltage readout uniquely determines a mirror angle, at least to within the limits of detection. In a more general case, it is sufficient that the curve be monotonically varying, to give a unique voltage-to-angle translation.

It should also be noted that while the default position of the moving element related to the zero target position is somewhat arbitrary, its selection may be constrained by the fact that the same element is often required, in practice, to also serve as a principal reflecting surface for interfacing with other optical subsystems, such as a treatment laser, a viewing microscope and/or a depth ranger. In the preferred embodiment employing a reflecting mirror as the movable optical element, the zero position angle is set at 45 degrees which provides a convenient interface with other system optics as well as superior resolution properties for measuring target displacements. In this case all mirror angle computations, such as the ones shown in FIG. 4, are calibrated relative to 45 degrees.

In general, the method of contrast tracking disclosed herein is independent of the type of moving optical element control. In alternate to embodiments of the invention, the motor drive may be based on either piezoelectric or electromagnetic principles. A piezoelectric driver uses the change In shape of a quartz crystal in response to a electric current to move the element. An electromagnetic driver uses a coil of wire In a magnetic field which is made to move by passing an electric current through the coil. The electromagnetic driver is similar in function to a voice coil of an audio speaker. In either case, the speed (or, more accurately, the acceleration) of the entire tracking system is limited by the response of the drivers and the mirror's moment of Inertia. In the preferred embodiment of the present invention, an electromagnetic drive using a voice coil means has been used successfully to reposition a mirror with high degree of accuracy (better than 10 microns) at accelerations of up to 40,000 deg/sec$^2$—sufficient to track even the fastest involuntary motions of the eye.

Figure 5:
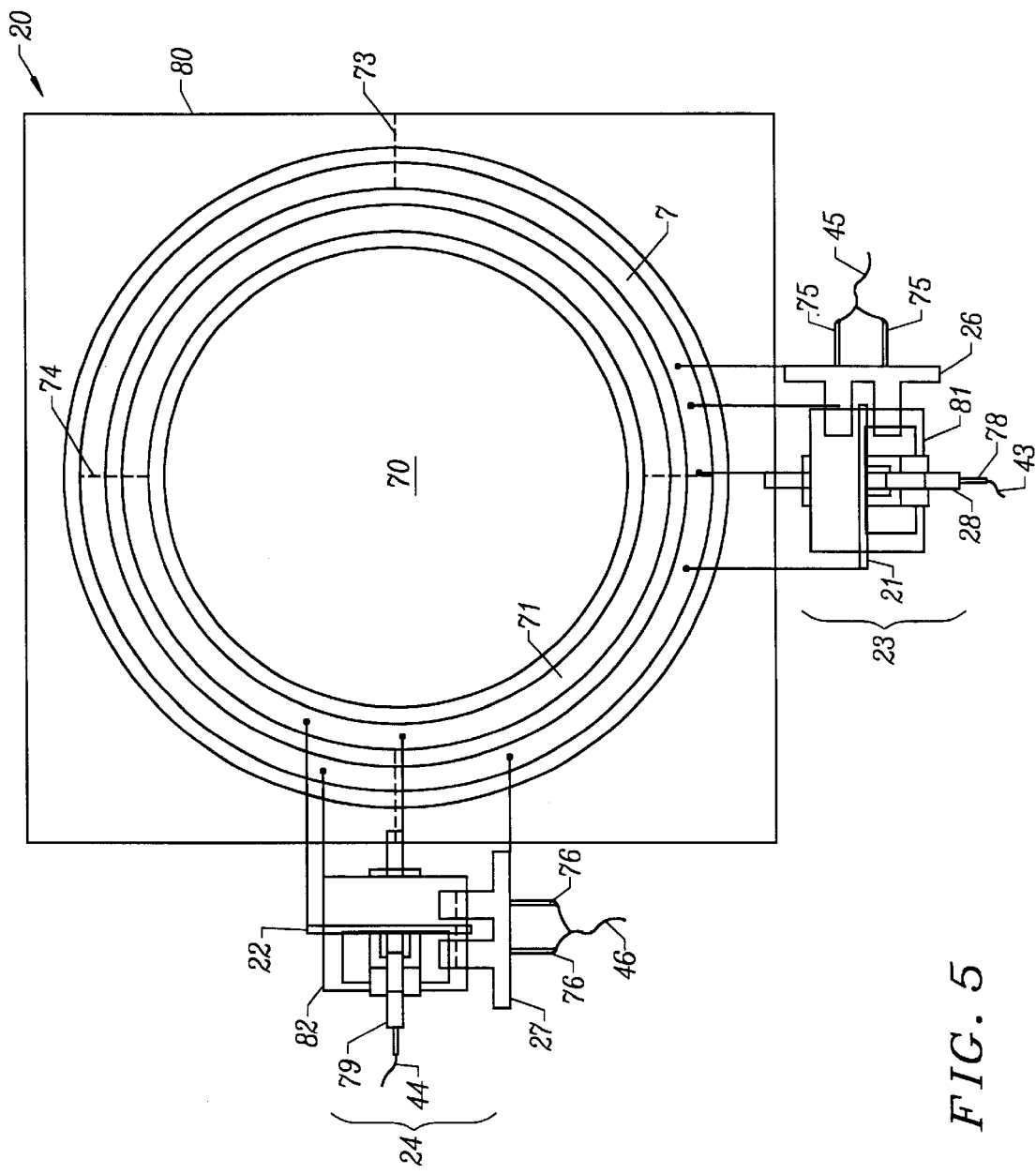
FIG. 5 is a front view of some key components of an X-Y mirror, used as the moving optical element in one preferred embodiment of the tracker.
Figure 5A:
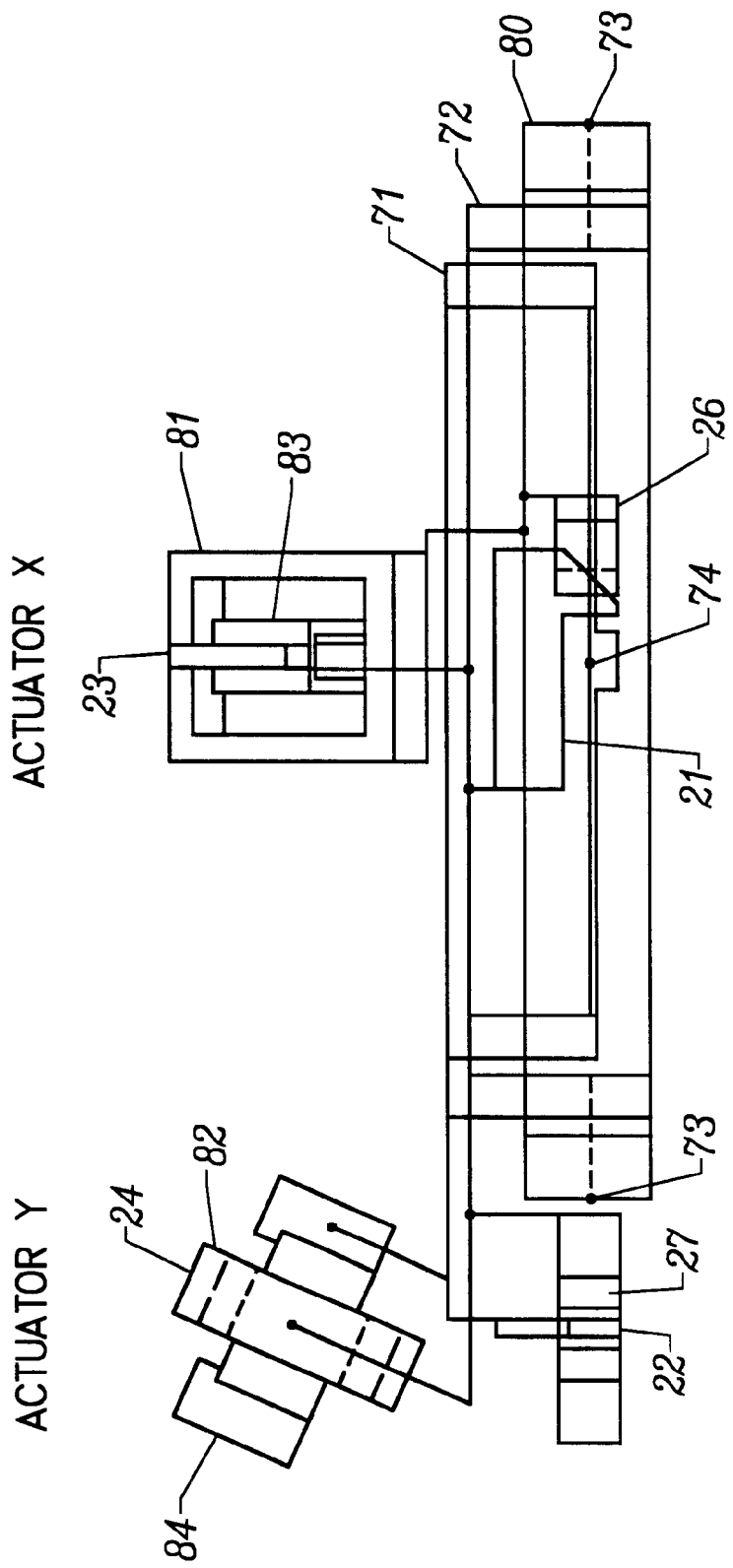
FIG. 5A is a side view of the same X-Y tracking mirror.

An example of a mirror assembly based on this type of control is shown in FIG. 5 with an expanded side view depicted in FIG. 5A, corresponding to a preferred embodiment of the invention. As illustrated in FIG. 5, the mirror 70 is mounted with two pivot axes—X and Y, indicated as 73 and 74, respectively. The outer gimbal ring 71 and the inner gimbal ring 72 allow the mirror to pivot about the X and Y axes respectively, as shown by the respective connections to the X and Y actuators 23 and 24. Each actuator consists of a stationary component, which is the permanent magnet frame (indicated as 81 and 82 for X and Y, respectively) and a dynamic component comprising the voice coil windings, also one for each axis. A better view of these dynamic components is obtained from the side view of FIG. 5A, where the windings are depicted in positions marked 83 and 84 respectively for the X and Y actuators. In the front view of FIG. 5 only the voice coil shuttles are seen in the locations marked 28 and 29. The sensors and the transducers (in this case, flags) comprise the other two components of the full mirror drive assembly. The sensors shown as 26 and 27 in FIGS. 5 and 5A, are stationary with respect to the actuators' permanent magnets while the flags 21 and 22 represent the dynamic components corresponding to the voice coil windings. Also shown in FIG. 5 are leads 75 and 76 linking the position sensors (or flags) to the X-Y logic board (via control lines 45 and 46, representing the same connections previousely shown in FIG. 1), and leads 78 and 79 which establish the electrical connections through which the servo drivers (designated 41 and 42 in FIG. 1) control the mirror actuators (i.e., relay lines 43 and 44 per FIG. 1).

Not indicated in FIGS. 5 and 5A are the mechanical stops which must be included to set a limit to the maximum movement of the mirror. In the preferred embodiment, where a mirror measuring about 13 mm in diameter is designed to track eye motions, setting this limit at about 5 degrees was found to be practical in most situations.

Intrinsic to any tracking scheme is the choice of what is to be tracked. If the target is a non-deformable body, then for the purposes of the system and methods of this invention, any landmark on or within the target would suffice for defining the motion of said material, as long as it be possessed of sufficient contrast and a degree of symmetry. However, for targets, including the eye, that neither move nor deform as a rigid body, it is also critical that the tracking landmark be located contiguous to the targeted tissue and should mechanically respond in a manner similar to the targeted tissue. At the same time, the tracking landmark should be sufficiently removed from the location of any other operations by the system of which the tracker is a part, so as to minimize potential interference from sources of light other than the illumination used for the present tracker. In the particular case of using the tracker to assist in laser Interventions, a further criterion for selection of the tracking landmark is that it be located at a target site not substantially affected by the laser procedure itself.

For example, in order to define the location of a moving tissue layer within the eye, any natural eye feature located in proximity of and structurally contiguous to the target site can serve as the tracking landmark as long as it has enough contrast, a degree of symmetry and be capable of responding to forces and pressures in a manner similar to the targeted tissues, yet without being coincident with the precise target site itself, since this site will change during the course of the surgery. For corneal procedures, including refractive surgery, the eye limbus at the radially outward edge of the cornea satisfies these constraints, providing sufficient contrast to allow the efficatious employment of the tracking methods discussed in this invention for a majority of the sighted patient population The limbus has the advantage of not only moving with the cornea—inasmuch as it is a part of the cornea—but, since it likewise is connected to the sclera, it will not respond as dramatically to the transient deformations associated with the microsurgery. A method for tracking the limbus has been disclosed by Knopp et. al. in U.S patent application Ser. No. 843,374 of which the present application is a continuation-in-part. This method employed a spatially sensitive sensor configuration comprising two quadrant detectors for which the limbus of the eye provided an ideally suited landmark. In particular, the two quadrant detector configuration presents a large enough area to intercept the light reflected from the large extent of the limbus structure of relatively (about 12 mm in diameter for humans; more than 15 mm in rabbits).

Figure 6:
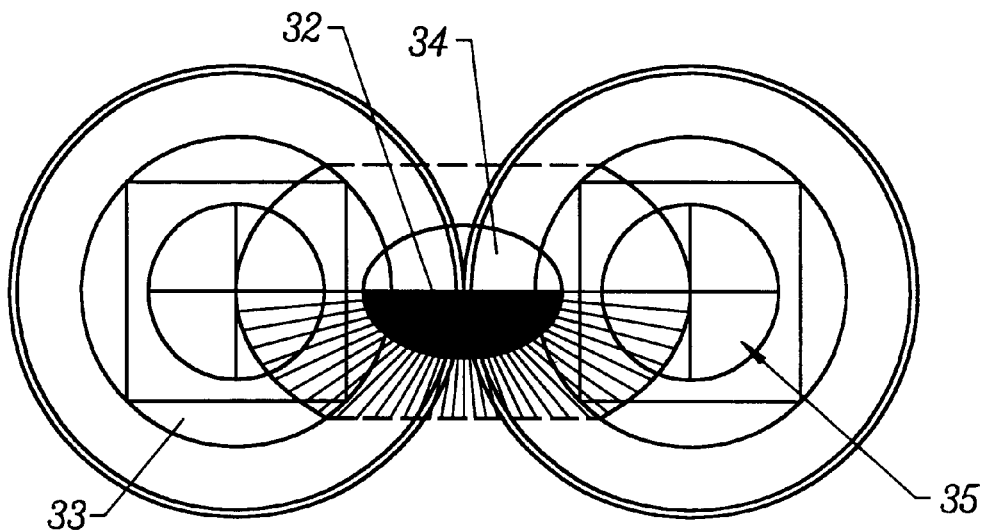
FIG. 6 shows an optical image of the iris, sclera and pupil of the eye, incident on a two quadrant detector configuration used as the position sensing detector in one preferred embodiment of the invention. Also indicated in FIG. 6 are the equations used to obtain the position signals when either one or both detectors are used.

For illustration, we reproduce, in FIG. 6, the method of detection used to track an image of the outer rim (at the limbus) of the iris as disclosed in the above mentioned patent application. This method is considered useful to one preferred embodiment of the present invention, applicable to ophthalmic surgical interventions, especially on or within the antertior segment of the eye, including the cornea. As shown in FIG. 6, the image at the two quadrant detectors (each with four quadrants, 35) consist of a bright luneshaped field 33 corresponding to the sclera 2, adjacent to a darker field representing an Image 32 of the iris 7. The very dark central core which is an image 34 of the pupil 68, is not captured by the detectors, leaving a single sharp contrast boundary to track. With each cell reacting separately to a given Illumination level, and the various cells of the quadrant detectors connected through differential amplifiers and normalized by the sum, the resultant signals are sensitive only to the position of the centrold of illumination pattern. Since quadrant detectors integrate the Image illumination striking each quadrant of the detector face, the photocurrents induced in the detector elements when normalized and subtracted according to the formulas shown in FIG. 6, will permit computation of the position of the light spot with respect to the center of the detector configuration. A change in background light intensity will be ignored, as the increase across the or eight quadrants 35 of the detector face will remain the same. Voltage sums and differences among the quadrants therefore serve to establish the relative direction of motion between two contiguous readings of the limbus position. A shift in intensity at the sensor is thereby traced to motion of the limbus.

As the equations of FIG. 6 indicate, the two detector configuration affords substantial flexibility to operations within the anterior segment, including the option of activating only one sensor at a time corresponding to detection of one side of the limbus, while allowing simultaneous operations to be performed adjacent to the other corner of the iris.

Also, it bears noting that the elliptical configuration of the illumination as shown in FIG. 6 can be deliberately selected (using cylindrical lenses) as one method to increase the sensitivity along the Y direction. Indeed, in the case of the eye, physical obstructions such as the eye lid prevent the addition of two more quadrant detectors in a direction perpendicular to the first set thereby achieving full symmetry. However, in a preferred embodiment, representing an improvement of the tracker over methods disclosed in U.S. patent application Ser. No. 843,374, spherical images (and hence Imaging lenses) may be used instead, as long as the light pattern is carefully tailored to highten the sensitivity along the perpendicular (Y) direction. Also, it is evident that a four quadrant detector configuration is an option that may be advantageously utilized in alternative embodiments for tracking other types of landmarks in applications that do not have the physical limitations imposed by the eye structure.

In application to corneal surgery, the methods of detection embodied in FIG. 6 and disclosed in patent application cited above, allowed a computerized control system to replicate a surgical template pattern selected on a user interface display to high accuracy, even though the eye surface may be appreciably deforming during the course of the surgical procedure. In particular, resolutions of better than a few microns were shown feasible with the quadrant detector configuration discussed above, for low magnifications and relatively short focal lengths (90–100 mm). Quadrant detectors also are known to be capable of recording voltage changes extremely rapidly and can thus observe and quantify contrast changes (and hence target motion) in less than 100 microseconds—sufficiently rapidly for the purpose of tracking all types of eye motion.

While clearly useful for corneal laser surgical procedures, quadrant detectors are not the only type of sensors compatible with the more general methods disclosed herein. The scope of the present invention is, in fact, broad enough to encompass a large number of possible targets and procedures and hence, a variety of tracking landmarks and detectors matched to sensing the contrasts thereof. Generally, as mentioned earlier, any feature pleasing sufficient contrast can curve as a tracking landmark, as long as it also has a minimal degree of symmetry. In the case of the cornea, or other anterior eye structures, such as the iris and the sclera, the pupil of the eye may also serve as a tracking mark. This despite the fact that the pupil may change its dimensions, since as long as the change is symmetrical and is not so fast as to exceed the response time of the sensors utilized, only relative illumination of different parts of the sensor(s) count in following the centroid of the illumination which is, in all cases, referenced to the center of the detectors' configuration. Thus, while not as attractive as the limbus for tracking the cornea, using the pupil as a landmark is understood to fall within the domain of the present disclosure whenever pure contrast-based alga rithms are utilized in the tracking. There may well be situations where tracking the pupil has certain advantages, such as when limited detection area; (relative to the much larger limbus) is desired, when the limbus contrast is inadequate, or if precise balance between the two spatial dimentions to be tracked is crucial.

Similarly, in other eye structures such as the retina, landmarks such as the optic disk, or vessel configurations (with suitably magnified views) can similarly provide landmarks upon which the present tracking method can be efficaciously deployed. Often, the primary modification required in choosing one particular feature to track upon over another, involves selection of alternate sensor configurations and the associated algorithms.

In general, for most types of tracking marks, the tracking sensors, or detectors, in combination with their circuitry, should have fast response times and be capable of high spatial resolutions. This is because target tracking landmarks such as the limbus are often not a boundary but a transition zone (e.g., between the cornea and the sclera). Therefore, a tracking system which uses the location of the limbus or similar such feature must be able to filter out noise, recognize contrast, and accomodate for shapes that may appear to deform due to rotations. The availability of advanced position-sensing photodetectors (PSD's) along with faster processing capabilities afforded by modern microprocessors can match these requirements with greater precision and reliability than was possible before. Examples of such advanced sensors are linear position sensing detectors and the quadrant detectors discussed above.

In the most general terms, a position sensing detection system works by sensing the angular deflection (or linear displacement) relative to a reference surface, or point, of a beam reflected off a moving element which is, in turn connected (optically) to the critically positioned target surface. With a dual element sensor the basic set-up provides a signal proportional to the deflection error around a single axis normal to the axial direction (or, more generally to a given line of sight). The polarity of the error indicates the direction of the error. The addition of a second channel normal in orientation to the first allows correction of angular errors about either axis in a plane normal to the optical axis (or line of sight). Quadrant detectors furnish a good example of a two-axis PSD. In a quadrant array, tour sensing elements are present on a single chip, which can therefore define position in two (X and Y) axes. With resolutions on the order of 0.1 urn and large detecting surfaces, quadrant detectors are highly suitable for precise centering and nulling and for position tracking of spatially extended features over narrow ranges.

Figure 7:
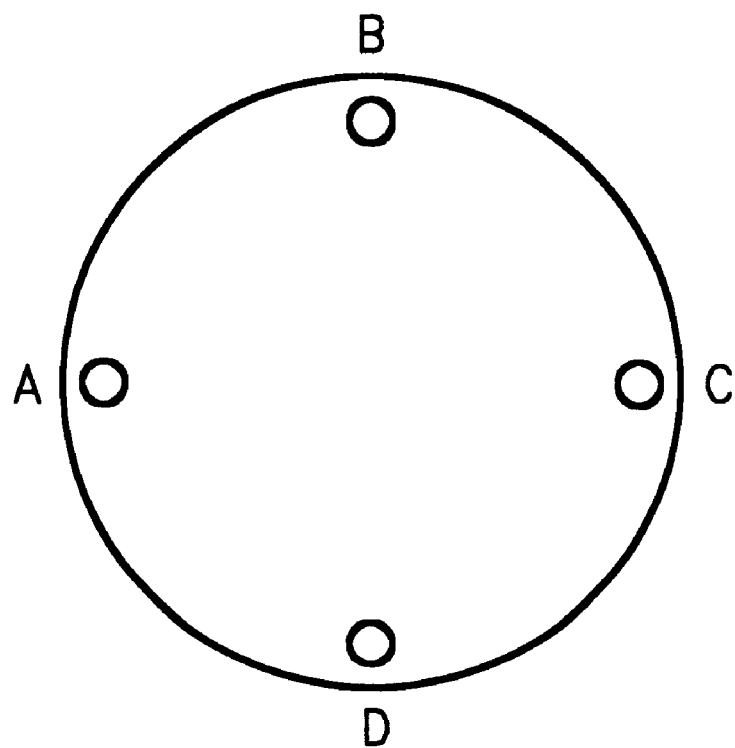
FIG. 7 illustrates another example of a sensor useful to the present invention, comprising, in this case, a lateral-effect detector configuration. The appropriate X and Y position signals are again indicated.

In alternate embodiments, similarly fast but more sensitive position sensing detectors may be used such as lateral-effect photodiodes, shown schematically in FIG. 7. These may be especially useful in applications, such as in industrial processing where measurements over wider ranges are required. This type of detector differs from the quadrant detector in that it comprises a single photodiode with continuous detection capability. This eliminates the "dead region" between the cells, and the signal outputs are directly proportional to the position of the centroid of light. In general, a two-axis lateral-effect diode acts as a pair of light-controlled variable resistors for measuring the position of a light spot on its X- and Y- coordinates, as illustrated by the equations in FIG. 7. Generally, this type of sensor provides good linearity over wider dynamic range than quadrant detector (within 3% over the entire range, on the avearge), which renders them more suitable for certain type of applications requiring great accuracy, such as in diagnostics. Also, it can be seen that, a linear position sensors such as the lateral-effect diode descibed here, may provide an excellent match for tracking alternative landmarks within the eye, such as the pupil, due to their smaller overasll area and the greater demands placed upon sensor linearity (relative to e.g., the limbus).

The above described preferred and alternate embodiments are intended to illustrate the principles of the invention but without limiting its scope. Other embodiments and variations to these preferred embodiments will be apparent to those skilled in the art and may be made without departing from the essence and scope of the invention as defined in the claims.

What is claimed is:

1. A system for tracking an eye of a living patient during laser eye surgery, the eye having a first feature and a second feature with a contrast border therebetween, the system comprising:

an illumination source oriented toward the eye to provide illumination light, the illumination light illuminating a first region of the eye extending across a first portion of the contrast border and including a first portion of the first feature and a first portion of the second feature of the eye, the illumination light also illuminating a second region of the eye extending across a second portion of the contrast border and including a second portion of the first feature and a second portion of the second feature;

a laser delivery optical train oriented toward the eye and adapted for receiving the illumination light reflected and scattered from the eye, the optical train focussing the scattered reflected light along an optical path to an image;

a photodetector system disposed in the optical path of the scattered reflected light from the optical train, the photodetector system generating a first signal and a second signal, the first signal indicating an integrated illumination of the focussed light from the first region of the eye, the second signal indicating an integrated illumination of the focussed light from the second region of the eye;

a processor coupled to the photodetector system to measure a lateral movement of the eye, by comparing the first signal to the second signal, and to produce an error signal from a difference between the first signal and the second signal which is normalized to ambient light using a sum of the first signal and the second signal; and a drive mechanism coupled to the processor to shift the optical train in response to the lateral movement of the eye so as to maintain alignment between the optical train and the eye.

2. A system as in claim 1, wherein the processor is adapted to produce an analog error signal using only analog signal processing.

3. A system as in claim 1, wherein the lateral movement of the eye derived by the processor is measured along an axis between the first and second regions of the eye.

4. A method for tracking an eye of a living body during laser eye surgery, the laser eye surgery comprising resculpting of a cornea effected by a corneal ablation laser, the eye having a first feature and a second feature with a contrast border therebetween, the method comprising:

illuminating first and second regions of the eye, each region extending across an associated portion of the contrast border from the first feature of the eye onto the second feature of the eye;

focussing scattered reflected light from each illuminated region of the eye with an optical train and detecting a first total amount of the focussed light from the first illuminated region of the eye and a second total amount of the focussed light from the second illuminated region of the eye;

generating an error signal when the eye moves laterally by determining a difference between the first detected amount of light and the second detected amount of light, and by normalizing the difference between the first and second detected amounts of light to ambient light; and shifting the optical train using the error signal so as to maintain alignment between the corneal ablation laser and the eye.

5. The method of claim 4, wherein the error signal generating step is performed using only analog signal processing.

6. The method as in claim 4, wherein the error signal is normalized using a combined total amount of detected light including the first detected amount of light and the second detected amount of light.

7. The method of claim 4, further comprising measuring the first and second detected amounts of light with first and second detectors, respectively, wherein each of the first and second detectors comprise structures selected from the group consisting of quadrant detectors, position sensing photodetectors, linear sensors, lateral-effect photodiodes, and single photodiodes with continuous detection capabilities.

8. The method of claim 4, wherein the first feature comprises an iris of the eye, wherein the second feature comprises a sclera of the eye, and wherein the contrast boundary comprises a limbus of the eye.

9. The method of claim 4, wherein the first feature comprises a pupil of the eye, wherein the second feature comprises an iris of the eye, and wherein the contrast boundary comprises an iris/pupil boundary of the eye.

10. The method of claim 4, further comprising preventing the laser from firing if the optics are not realigned.

* * * * *